(12) United States Patent
Kim et al.

(10) Patent No.: US 9,375,182 B2
(45) Date of Patent: Jun. 28, 2016

(54) SYSTEM AND METHOD FOR ACQUISITION OF BIOPOTENTIAL SIGNALS WITH MOTION ARTIFACT REDUCTION

(71) Applicant: IMEC VZW, Leuven (BE)

(72) Inventors: Hyejung Kim, Leuven (BE); Nick Van Helleputte, Korbeek Dijle (BE); Refet Firat Yazicioglu, Leuven (BE)

(73) Assignee: IMEC VZW, Leuven (BE)

( * ) Notice: Subject to any disclaimer, the term of this patent is extended or adjusted under 35 U.S.C. 154(b) by 0 days.

(21) Appl. No.: 14/573,714

(22) Filed: Dec. 17, 2014

(65) Prior Publication Data

US 2015/0173683 A1 Jun. 25, 2015

(30) Foreign Application Priority Data

Dec. 23, 2013 (EP) .................................. 13199276
Feb. 20, 2014 (EP) .................................. 14156018

(51) Int. Cl.
*A61B 5/04* (2006.01)
*A61B 5/00* (2006.01)
*A61B 5/0428* (2006.01)
*A61B 5/0402* (2006.01)

(52) U.S. Cl.
CPC ............ *A61B 5/7207* (2013.01); *A61B 5/0402* (2013.01); *A61B 5/04017* (2013.01); *A61B 5/0428* (2013.01); *A61B 5/7214* (2013.01); *A61B 5/7246* (2013.01)

(58) Field of Classification Search
None
See application file for complete search history.

(56) References Cited

U.S. PATENT DOCUMENTS

2008/0033266 A1    2/2008   Diab et al.

FOREIGN PATENT DOCUMENTS

| EP | 2561805 A1 | 2/2013 |
| EP | 2591720 A1 | 5/2013 |

OTHER PUBLICATIONS

Kim, Sunyoung et al., "Real Time Digitally Assisted Analog Motion Artifact Reduction in Ambulatory ECG Monitoring System", 34th Annual International Conference of the IEEE EMBS, San Diego, California USA, Aug. 28-Sep. 1, 2012, pp. 2096-2099.
International Search Report for 14156018.5-1506 dated Oct. 4, 2014.
Buxi, Dilpreet et al., "Correlation between Electrode-Tissue Impedance and Motion Artifact in Biopotential Recordings", IEEE Sensors Journal, vol. 12, No. 12, Dec. 2012, pp. 3373-3383.
Khambete, N.D., et al., "Movemenet Artefact Rejection in Impedance Pneumography Using Six Strategically Placed Electrodes", Physiol. Meas. 21 (2000), pp. 79-89.
Kim, Hyejung et al., "Motion Artifact Removal Using Cascade Adaptive Filtering for Ambulatory ECG Monitoring System", pp. 160-163.

*Primary Examiner* — Brian T Gedeon
*Assistant Examiner* — Ankit D Tejani
(74) *Attorney, Agent, or Firm* — McDonnell Boehnen Hulbert & Berghoff LLP

(57) ABSTRACT

A biopotential signal acquisition system including an analog readout unit configured to receive an analog biopotential signal, which may be acquired from at least one electrode attached to a body; and to extract an analog measured biopotential signal and an analog reference signal. The system also includes an ADC unit configured to provide a digital version of the analog measured biopotential signal and the analog reference signal, a digital filter unit configured to calculate a digital motion artifact estimate based on the digital version of the measured biopotential signal and the reference signal. The system further comprises a reference signal processing unit configured to convert the reference signal into a new reference signal being provided to the digital filter unit based on the correlation between the measured biopotential signal and the reference signal.

20 Claims, 3 Drawing Sheets

SYSTEM AND METHOD FOR ACQUISITION OF BIOPOTENTIAL SIGNALS WITH MOTION ARTIFACT REDUCTION

CROSS-REFERENCE TO RELATED APPLICATIONS

This application claims priority to European Patent Application Nos. 13199276.0 filed Dec. 23, 2013, and 14156018.5 filed Feb. 20, 2014, the contents of each of which are hereby incorporated by reference.

TECHNICAL FIELD

The present disclosure relates generally to the field of biopotential signal acquisition systems and more specifically to a system and a method for acquisition of biopotential signals with motion artifact reduction using digital adaptive filtering.

SUMMARY

Ambulatory monitoring of biopotential signals, such as electrocardiogram (ECG), electroencephalogram (EEG), electromyogram (EMG), etc., is a highly relevant topic in personal healthcare. A key technical challenge in such application environments is overcoming motion artifacts that significantly affect the recorded biopotential signals. An approach to reduce motion artifacts is by using digital adaptive filtering. For example, a known biomedical acquisition system with motion artifact reduction is disclosed in EP 2 591 720 A1, which uses digital adaptive filtering (e.g. a LMS filter), implemented in a digital domain, to calculate a motion artifact estimate which is then fed back to the analogue domain and subtracted from the measured ECG before final amplification. Another known technique for motion artifact removal using a two-stage cascade LMS adaptive filter is disclosed in the document "*Motion Artifact Removal using Cascade Adaptive Filtering for Ambulatory ECG Monitoring System*", by Hyejung Kim et al., Biomedical Circuits and Systems Conference (BioCAS), November 2012 IEEE, Hsinchu, Taiwan.

SUMMARY

According to one aspect of the present disclosure, a new biopotential signal acquisition system is provided with improved motion artifact reduction. According to another aspect, the disclosure is advantageous for ambulatory and/or low power biopotential monitoring applications.

According to an example embodiment, there is provided a biopotential signal acquisition system including an analogue readout unit configured to receive an analogue biopotential signal and to extract, from that received analogue biopotential signal, an analogue measured biopotential signal and an analogue reference signal. The system also includes an ADC unit configured to provide a digital version of the analogue measured biopotential signal and the analogue reference signal, and a digital filter unit configured to calculate a digital motion artifact estimate based on the digital version of the measured biopotential signal and the reference signal. The system further comprises a reference signal processing unit configured to convert the reference signal into a new reference signal being provided to the digital filter unit based on the correlation between the measured biopotential signal and the reference signal. The received analogue biopotential signal may be acquired, for example, from at least one electrode attached to a living being's body.

According to an example embodiment, the correlation between the measured biopotential signal and the reference signal may be estimated by calculating the correlation between the motion artifact estimate signal and the reference signal.

According to an example embodiment, the correlation between the measured biopotential signal and the reference signal may be estimated by calculating the correlation between the analogue biopotential signal and the reference signal.

According to an example embodiment, the polarity of the new reference signal may be calculated based on the correlation between the measured biopotential signal and the reference signal. The polarity of the new reference signal may be the same or opposite to the polarity of the reference signal depending on the correlation between the measured biopotential signal and the reference signal.

According to an example embodiment, the reference signal processing unit may be implemented in an analogue domain part or digital domain part of the system.

According to an example embodiment, the digital filter unit may implement or runs a digital adaptive filter, such as, for example an LMS filter.

According to an example embodiment, the reference signal may be an electrode-tissue impedance signal. According to an example embodiment, the analogue biopotential signal may be an ECG signal.

There is also provided an electronic device comprising a biopotential signal acquisition system according to any of the embodiments herein described.

There is also provided a method for acquisition of biopotential signals. The method includes extracting, from an analogue biopotential signal, an analogue measured biopotential signal and an analogue reference signal, converting the reference signal into a new reference signal based on the correlation between the measured biopotential signal and the reference signal, and calculating a digital motion artifact estimate based on the digital version of the measured biopotential signal and the new reference signal.

Certain objects and advantages of various new and inventive aspects have been described above. It is to be understood that not necessarily all such objects or advantages may be achieved in accordance with any particular embodiment of the present disclosure. Those skilled in the art will recognize that the solution of the present disclosure may be embodied or carried out in a manner that achieves or optimizes one advantage or group of advantages without necessarily achieving other objects or advantages.

BRIEF DESCRIPTION OF THE DRAWINGS

The above and other aspects of the system and method for acquisition of biopotential signals according to the present disclosure will be shown and explained with reference to the non-restrictive example embodiments described hereinafter.

DETAILED DESCRIPTION

In the following description of example embodiments, various features may be grouped together in a single embodiment, figure, or description thereof for the purpose of streamlining the disclosure and aiding in the understanding of one or more of the various inventive aspects. This is however not to be interpreted as the disclosure requiring more features than the ones expressly recited in the main claim. Furthermore, combinations of features of different embodiments are meant to be within the scope of the disclosure, as would be clearly understood by those skilled in the art. Additionally, in other instances, well-known methods, structures and techniques have not been shown in detail in order not to obscure the conciseness of the description.

Figure 1:
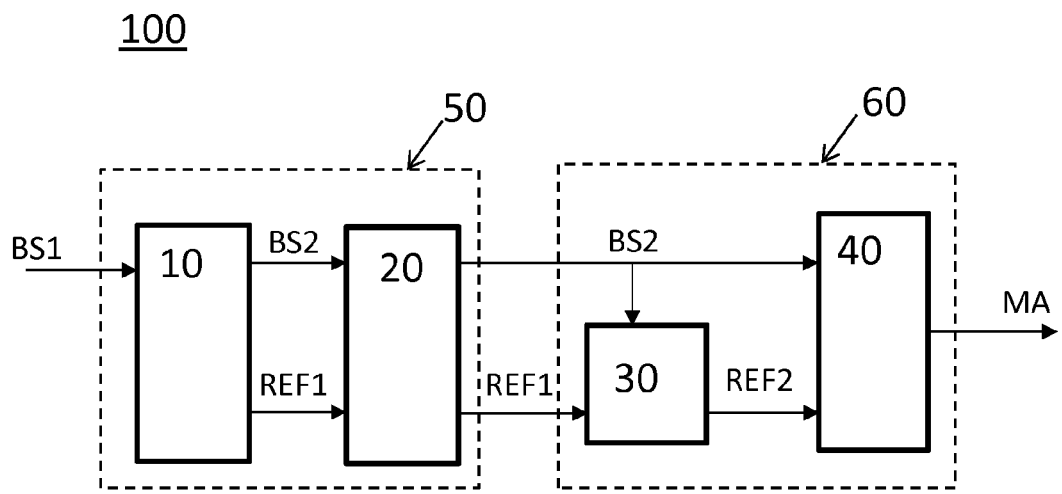
FIG. 1 shows a first example block diagram of a biopotential signal acquisition system according to an embodiment of the disclosure.

FIG. 1 shows a first example block diagram of a biopotential signal acquisition system 100 according to an embodiment of the disclosure. The system comprises an analogue domain part 50 configured to receive at least one analogue biopotential signal BS1, which may be acquired, for example, from at least one sensor electrode attached to a living being body, and comprises an analogue readout unit 10 which extracts at least one analogue measured biopotential signal BS2 and at least one analogue reference signal REF1. The analogue measured biopotential signal BS2 and the analogue reference signal REF1 are then provided to an analogue-to-digital converter (ADC) unit 20, which comprises one or more ADCs configured to convert those signals into digital versions which are then handled in the digital domain part 60 of the system. A reference signal processing unit 30 receives the digital versions of the measured biopotential signal BS2 and the reference signal REF1 and is configured to calculate a correlation between both signals and generate a new reference signal REF2 based on the value of that correlation. A digital filter unit 40 receives the measured biopotential signal BS2 and the new reference signal REF2 and calculates an estimated noise or motion artifact estimate MA, which is used to reduce the motion artifact from the measured biopotential signal.

According to an example embodiment, the reference signal processing unit 30, based on the correlation value between the measured biopotential signal BS2 and the reference signal REF1, checks the polarity between both signals and adapts the reference signal REF1 based on such polarity value. If the polarity information has a first value, indicating that the reference signal REF1 has the same polarity as the measured biopotential signal BS2, then the reference signal processing unit 30 provides a signal REF2 that is the same as reference signal REF1 to the digital filter unit 40. If the polarity information has a second value, indicating that the reference signal REF1 has an opposite polarity than the measured biopotential signal BS2, then the reference signal processing unit 30 provides a signal REF2 that has polarity opposite to the polarity of the reference signal REF1.

According to an example embodiment, the correlation value between the measured biopotential signal BS2 and the reference signal REF1 is calculated continuously. According to an example embodiment, the correlation value varies between a maximum value, e.g. +1, in the case of a perfect positive (increasing) linear relationship (correlation) and a minimum value, e.g. −1, in case of a perfect decreasing (negative) linear relationship (anti-correlation), depending on the degree of linear dependence between the signals. The polarity calculation is then performed by comparing the calculated correlation value with a certain threshold value, which can be a certain predefined value or dynamically calculated. According to an example embodiment, in case the calculated correlation value is equal to and/or greater than a certain threshold value, the polarity value is given a first value, e.g. 0, and in case the calculated correlation value is equal to and/or lower than a certain threshold value, the polarity value is given a second value, e.g. 1. According to an example embodiment, once the polarity value is updated, it is maintained for a certain period of time in order to avoid oscillation.

According to an example embodiment, the reference signal processing unit 30 generates a new reference signal REF2, which is an adaptation of the received reference signal REF1. By using the polarity information, the new reference input REF2 for the digital filter unit 40 is generated. The new reference signal REF2 is the same as the received reference signal REF1 in case the received reference signal REF1 has the same polarity as the measured biopotential signal BS2, and the new reference signal REF2 is a signal that has polarity opposite to the polarity of the reference signal REF1 in case the received reference signal REF1 has an opposite polarity than the measured biopotential signal BS2.

According to an example embodiment, the correlation value between the measured biopotential signal BS2 and the reference signal REF1 may be also estimated by calculating the correlation between the estimated noise signal or motion artifact estimate MA at the output of the digital filter unit 40 and the reference signal REF1. According to another example embodiment, the correlation value between the measured biopotential signal BS2 and the reference signal REF1 may be estimated by calculating the correlation between the analogue biopotential signal BS1 and the reference signal REF1.

Advantageously, according to an example embodiment of the disclosure, the new reference signal REF2 has higher correlation with the measured biopotential signal BS2, which improves the performance of the digital filter unit 40 for calculation of the motion artifact estimate MA. In consequence, the motion artifact estimate MA can be calculated faster and with more accuracy, which in turn improves motion artifact reduction.

According to an example embodiment, the biopotential signal acquisition system 100 works in real-time.

According to an example embodiment, the analogue biopotential signal BS1 is an electrocardiogram signal and the reference signal REF1 is an electrode-tissue impedance signal.

According to an example embodiment, the digital filter unit 40 may implement or run a digital adaptive filter, for example, a Least Mean Square (LMS) filter. According to an example embodiment, the reference signal processing unit 30 may be implemented as part of the digital filter unit 40, for example, as part of the LMS filter. The digital filter unit 40 and the reference signal processing unit 30 may be implemented in hardware and/or software, in a dedicated digital domain part 60 and in the same chip as the analogue part 50. According to an example embodiment, the digital filter unit 40 and the reference signal processing unit 30 may be implemented in hardware and/or software in an off-chip or external microcontroller or microprocessor.

According to one example embodiment, all the modules shown in FIG. 1 may be integrated on a single chip. This is advantageous for example to reduce the group delay for real time solution and/or to reduce the power consumption.

Figure 2:
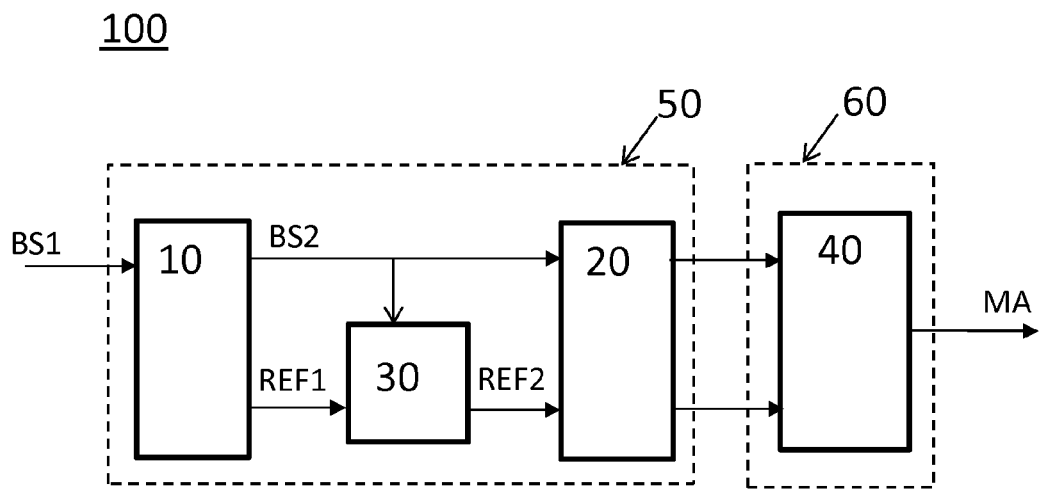
FIG. 2 shows a second example block diagram of a biopotential signal acquisition system according to an embodiment of the disclosure.

FIG. 2 shows a second example block diagram of a biopotential signal acquisition system 100 according to an embodiment of the disclosure. Basically the same working principle as the one explained with regard to FIG. 1 applies, but for the fact that now the reference signal processing unit 30 is implemented in the analogue domain part 50 and adapts the reference signal REF1 in such domain.

Figure 3:
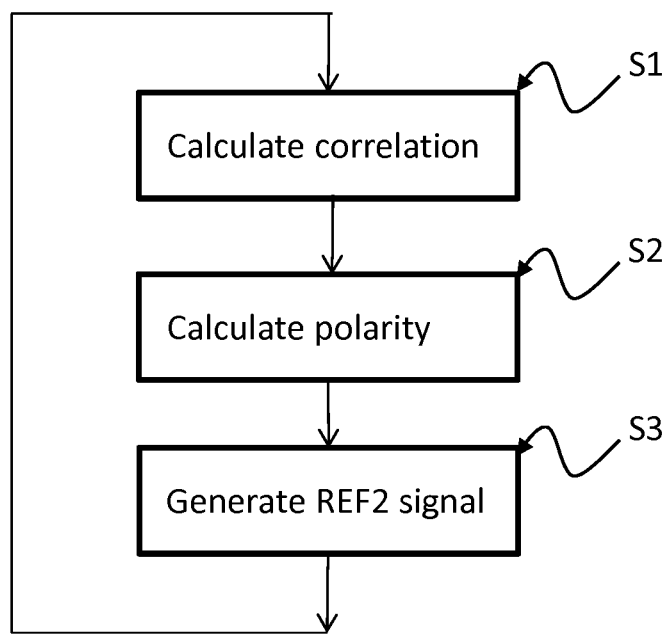
FIG. 3 shows a flow diagram of a method for the acquisition of biopotential signals according to an embodiment of the disclosure.

FIG. 3 shows a simplified flow diagram of a method for acquisition of biopotential signals with motion artifact reduction according to an embodiment of the disclosure. The method comprises, in a first step S1, calculating the correlation between a measured biopotential signal BS2 and a reference signal REF1; in a second step S2, calculating the polarity between the measured biopotential signal BS2 and the reference signal REF1; and, in a third step S3, generating a new reference signal REF2 which is provided to a digital filter unit for motion artifact estimation.

According to an example embodiment, the correlation value between a measured biopotential signal BS2 and the reference signal REF1 is calculated in a first step S1. This may be done, in example implementations, continuously and with a certain sampling rate in order to reduce the active power consumption. According to example implementations, the estimated motion artifact signal MA may be also used for calculating the correlation value according to the equation:

$$corr_j = \frac{(dataIn\_A_j - \overline{dataIn\_A_{j-31:\,j}}) \cdot (dataIn\_B_j - \overline{dataIn\_B_{j-31:\,j}})}{32}$$

Wherein dataIn_A is the motion artifact estimate signal MA, dataIn_B is the reference signal REF 1, and corr is the correlation value. The sampling rate (32) may be changed and is a design option.

According to an example embodiment, the correlation value may be +1 in the case of a perfect positive (increasing) linear relationship (correlation), and −1 in the case of a perfect decreasing (negative) linear relationship (anti-correlation), and some value between −1 and 1 in all other cases, indicating the degree of linear dependence between the variables. As it approaches zero there is less of a relationship (closer to uncorrelated).

According to an example embodiment, after calculating the correlation value, a polarity calculation may be performed, for example as a polarity change request signal, req_p, which is generated as the following equation:

$$req\_p_j = \begin{cases} 0, & \sum corr \geq CORR\_TH \\ 1, & \sum corr < CORR\_TH \end{cases}$$

Where corr is the correlation value and CORR_TH is a certain threshold value. To avoid oscillation, once the polarity is updated, it may stay for a certain period of time, for example at least for 1 second. This period of time can be programmed and is a design option.

According to an example embodiment, by using polarity information, the new reference input REF2 for the digital filter is updated as in the following equations:

$$ref_{neg} = REF\_OFF \times 2 - ref_{pos}$$

$$ref_{new} = \begin{cases} ref_{pos}, & polarity = 0 \\ ref_{neg}, & polarity = 1 \end{cases}$$

Where $ref_{pos}$ is the reference input, $ref_{neg}$ is the reference signal with opposite polarity and $ref_{new}$ is the new reference signal REF2. REF_OFF is a reference offset, which may be designed according to the acquisition environment such as subject, type of electrode, quality of electrode, etc., and its value may be adjusted at the beginning, and updated regularly during the operation.

Figure 4:
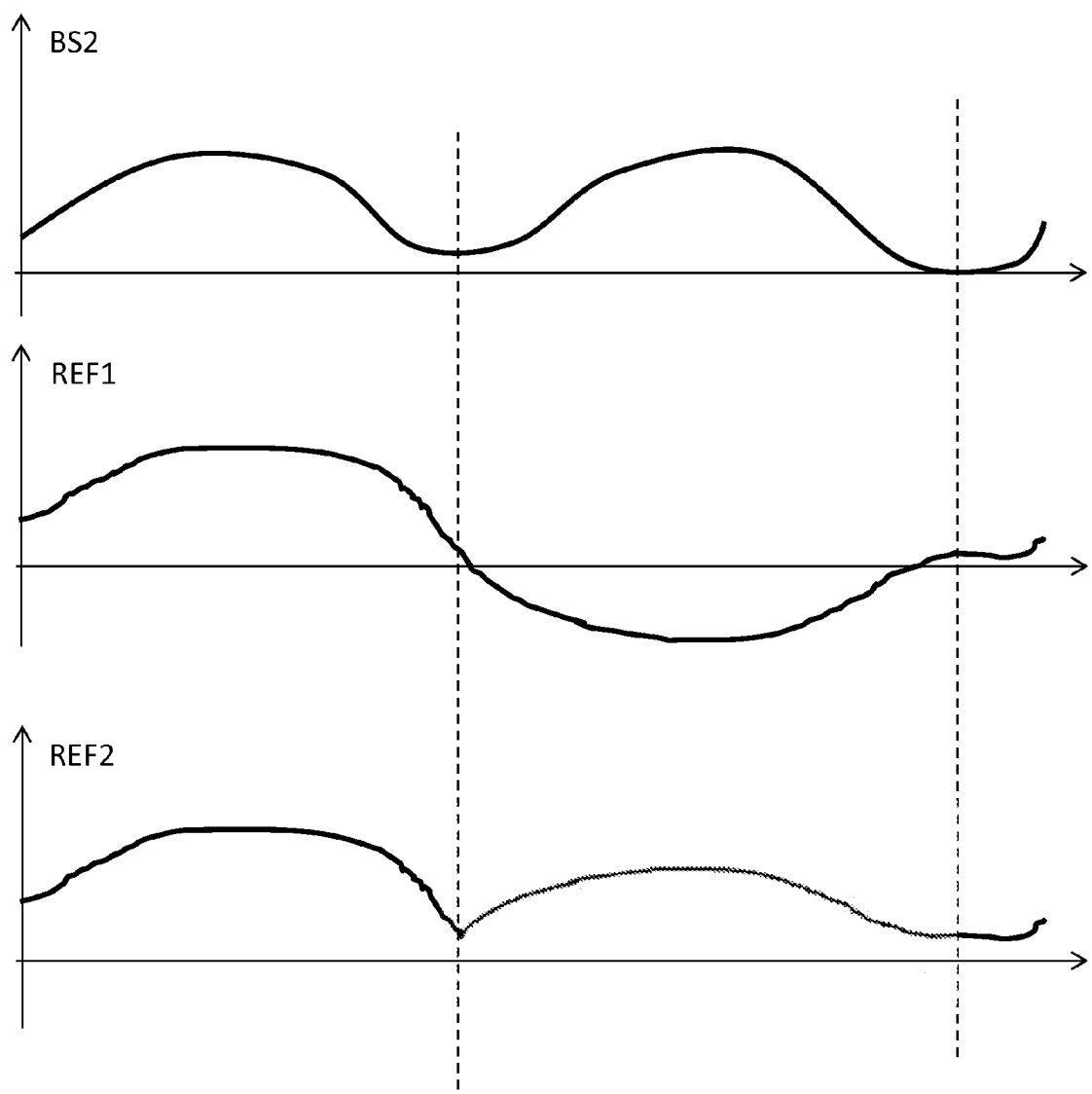
FIG. 4 illustrates example graphs of signals generated in a biopotential signal acquisition system according to an embodiment of the disclosure.

FIG. 4 illustrates example graphs of the measured biopotential signal BS2, the reference signal REF1 and the new reference signal REF2 generated in a biopotential signal acquisition system according to an embodiment of the disclosure. As illustrated in the figure, the new reference signal REF2 is an adaptation of the reference signal REF1, in which the polarity of the reference signal REF1 changed such that it has a higher correlation with the measured biopotential signal BS2.

The invention claimed is:

1. A biopotential signal acquisition system comprising:
   a readout unit configured to receive an analogue biopotential signal and to extract, from that received analogue biopotential signal, a measured biopotential signal and a first reference signal;
   a reference signal processing unit configured to convert the first reference signal into a second reference signal based on a correlation between the measured biopotential signal and the first reference signal; and
   a digital filter unit configured to calculate a digital motion artifact estimate based on a digital version of the measured biopotential signal and the second reference signal,
   wherein the correlation between the measured biopotential signal and the first reference signal is estimated by calculating a correlation between the digital motion artifact estimate and the first reference signal.

2. The biopotential signal acquisition system according to claim 1, wherein the correlation between the measured biopotential signal and the first reference signal is estimated by calculating the correlation between the digital motion artifact estimate and a digital version of the first reference signal.

3. The biopotential signal acquisition system according to claim 1, wherein a polarity of the second reference signal is calculated based on the correlation between the measured biopotential signal and the first reference signal.

4. The biopotential signal acquisition system according to claim 3, wherein the polarity of the second reference signal is the same or opposite to a polarity of the first reference signal depending on the correlation between the measured biopotential signal and the first reference signal.

5. The biopotential signal acquisition system according to claim 1, wherein the reference signal processing unit is implemented in an analogue domain part of the system.

6. The biopotential signal acquisition system according to claim 1, wherein the reference signal processing unit is implemented in a digital domain part of the system.

7. The biopotential signal acquisition system according to claim 1, wherein the digital filter unit implements or runs a digital adaptive filter.

8. The biopotential signal acquisition system according to claim 7, wherein the digital adaptive filter is a Least Mean Square (LMS) filter.

9. The biopotential signal acquisition system according to claim 1, wherein the first reference signal is an electrode-tissue impedance signal.

10. The biopotential signal acquisition system according to claim 1, wherein the analogue biopotential signal is an ECG signal.

11. An electronic device comprising a biopotential signal acquisition system according to claim 1.

12. A method for acquisition of biopotential signals, comprising:
extracting, from an analogue biopotential signal, a measured biopotential signal and a first reference signal;
converting the first reference signal into a second reference signal based on a correlation between the measured biopotential signal and the first reference signal;
calculating a polarity of the second reference signal based on the correlation between the measured biopotential signal and the first reference signal; and
calculating a digital motion artifact estimate based on a digital version of the measured biopotential signal and the second reference signal.

13. The method for acquisition of biopotential signals of claim 12, herein the first reference signal is an electrode-tissue impedance signal and the analogue biopotential signal is an ECG signal.

14. The method for acquisition of biopotential signals of claim 12, wherein the polarity of the second reference signal is the same or opposite to a polarity of the first reference signal depending on the correlation between the measured biopotential signal and the first reference signal.

15. The method for acquisition of biopotential signals of claim 12, further comprising:
calculating a correlation between the digital motion artifact estimate and the first reference signal; and
estimating the correlation between the measured biopotential signal and the first reference signal based on the calculated correlation between the digital motion artifact estimate and the first reference signal.

16. A biopotential signal acquisition system comprising:
a readout unit configured to receive an analogue biopotential signal and to extract, from the received analogue biopotential signal, a measured biopotential signal and a first reference signal;
a reference signal processing unit configured to convert the first reference signal into a second reference signal based on a correlation between the measured biopotential signal and the first reference signal, and to calculate a polarity of the second reference signal based on the correlation between the measured biopotential signal and the first reference signal; and
a digital filter unit configured to calculate a digital motion artifact estimate based on the measured biopotential signal and the second reference signal.

17. The biopotential signal acquisition system according to claim 16, wherein the polarity of the second reference signal is the same or opposite to a polarity of the first reference signal depending on the correlation between the measured biopotential signal and the first reference signal.

18. The biopotential signal acquisition system according to claim 16, wherein the reference signal processing unit is implemented in a digital domain part of the system.

19. The biopotential signal acquisition system according to claim 16, wherein the digital filter unit implements or runs a digital adaptive filter.

20. The biopotential signal acquisition system according to claim 16, wherein the first reference signal is an electrode-tissue impedance signal, and the analogue biopotential signal is an ECG signal.

* * * * *